United States Patent
Reddy

(10) Patent No.: US 9,663,438 B2
(45) Date of Patent: May 30, 2017

(54) PROCESS FOR FORMING CHROMIUM PROPIONATE AS AN AGRICULTURAL FEED ADDITIVE

(71) Applicant: Pratap V Reddy, Fayetteville, NY (US)

(72) Inventor: Pratap V Reddy, Fayetteville, NY (US)

(73) Assignee: NuTech Biosciences, Inc., Oneida, NY (US)

( * ) Notice: Subject to any disclaimer, the term of this patent is extended or adjusted under 35 U.S.C. 154(b) by 0 days.

(21) Appl. No.: 14/845,452

(22) Filed: Sep. 4, 2015

(65) Prior Publication Data

US 2017/0066707 A1    Mar. 9, 2017

(51) Int. Cl.
*A23L 1/29* (2006.01)
*C07C 51/41* (2006.01)
*A23K 1/175* (2006.01)

(52) U.S. Cl.
CPC .......... *C07C 51/418* (2013.01); *A23K 1/1758* (2013.01)

(58) Field of Classification Search
CPC ..... C07C 51/418; C01B 3/0026; A23K 10/00; A23K 20/20; A23K 10/40
USPC .......................................... 426/74, 648, 807
See application file for complete search history.

(56) References Cited

U.S. PATENT DOCUMENTS 5,707,679 A * 1/1998 Nelson .................. C07C 51/412
426/635

* cited by examiner

*Primary Examiner* — Helen F Heggestad
(74) *Attorney, Agent, or Firm* — Bernhard P. Molldrem, Jr.

(57) ABSTRACT

Chromium propionate, as an animal feed supplement, is created employing chromium carbonate and propionic acid as starting materials. A quantity of chromium carbonate is dissolved into water and propionic acid is stirred in to this, followed by calcium oxide. The propionic acid reacts with the chromium carbonate to form chromium propionate. The calcium oxide minimizes the hygroscopic nature of the finished product, to prevent caking and lumping. The chromium propionate appears as a precipitate, which is dried and can be centrifuged to drive out excess propionic acid. The dried precipitate is delumped and ground to a desired particle size. The end product has a minimum of 10% active bio-available chromium(III) content.

10 Claims, No Drawings

PROCESS FOR FORMING CHROMIUM PROPIONATE AS AN AGRICULTURAL FEED ADDITIVE

BACKGROUND OF THE INVENTION

The present invention concerns processes for generating trivalent chromium compounds and/or chelates that can be added to animal feeds to provide chromium as an essential trace metal in the animal's diet. This assists in metabolic uptake of glucose, and can boost weight gain in cattle, hogs, sheep, and poultry.

Various processes have been proposed for providing trivalent chromium, and several proposals have been offered for techniques to synthesize chromium propionate as well as other polyvalent metal propionates. Typically the starting materials have been hexavalent chromium compounds, where the chromium needed to be converted first into trivalent form before it could be used as a feed supplement. This typically required a reducing step in which a reducing agent such as a nitrite contacts the chromium source material to convert it from chromium(VI) to chromium(III).

These earlier processes involve heating the materials and require a catalyst to convert the chromium from the hexavalent state to trivalent chromium.

OBJECTS AND SUMMARY OF THE INVENTION

It is an object of this invention to provide a process that yields bio-available Cr(III) suitable for use as a feed additive, and which avoids the drawbacks of the prior art.

It is another object to provide a process for producing chromium propionate that avoids reliance on a catalyst or on added external heat.

Another object is to provide a process in which the end product contains a minimum of 10% available chromium.

According to one aspect of the present invention, chromium propionate is produced in a suitable form for use as an agricultural feed additive containing a minimum of 10% available chromium(III). In the process chromium carbonate, $Cr_2(CO_3)_3$ is used as a starting material rather than chromium oxide or chromium chloride. A quantity of chromium carbonate is placed into a vessel and water is added and stirred to form a paste. This step is carried out at room temperature. Then propionic acid, $CH_3CH_2COOH$, is added with continuous stirring. After these are well mixed, calcium oxide CaO is added in to raise the pH of the paste, also with constant stirring which is continued until there are no visible remaining particles of CaO. This may typically take about 15 minutes for a batch where the starting materials include about a quarter-liter of water. The reaction of propionic acid and chromium carbonate is exothermic, and the heat of reaction will evaporate most of the water from the precipitate. After this, the precipitate is transferred to a drying device, e.g., a centrifuge to remove the remaining water and with it any unreacted acid. Drying time varies from one device to another. The dried materials are then ground or otherwise comminuted to a suitable particle size for adding to the animal feed. The calcium oxide in the product serves as an anti-caking agent to ensure that the chromium propionate powder remains free flowing. The CaO minimizes the hygroscopic nature of the finished product and also raises the pH of the product to balance its acidic nature. Other agents, such as magnesium oxide can be substituted for the calcium oxide, although the free-flowing characteristics of the finished product may be affected.

The product thus formed has a minimum active chromium content of ten percent.

In a scaled-up process, either batch or continuous process, the starting material would include chromium carbonate in an amount of about 1,000 g to 1,200 g per each liter of water, and the propionic acid is added in an amount that is molar equivalent to the chromium carbonate. This can mean that the propionic acid is added in an amount of about 2,300 g per each liter of water. Then calcium oxide would be added in an amount of about 900 g per each liter of water.

The ingredients are reacted until completion, dried, and centrifuged to remove excess water and excess propionic acid. The dried precipitate is ground to a desired particle size and it is then ready to be blended with animal feed to supply the animals with available chromium.

The foregoing and many other objects, features, and advantages of this invention will be more fully understood from the following detailed description of a preferred embodiment.

DETAILED DESCRIPTION OF A PREFERRED EMBODIMENT

The process according to an embodiment of the invention is carried out at standard room temperature, i.e., does not require added heat. The process heat generated by the exothermic reaction is sufficient. Also, unlike other processes for generating trivalent chromium, this process does not employ sodium hydroxide to adjust pH or as a catalytic agent. No organic solvents are required or employed in the process.

The process can be concisely described as follows: a fixed quantity of chromium carbonate is dissolved into a known quantity of water. To this propionic acid is added with constant stirring. Following that, calcium oxide is added, which will moderate the acidity of the product and will also minimize the hygroscopic nature of the chromium propionate finished product. Up to this point the reaction of the starting materials is exothermic, and no external heating needs to be employed.

The chromium propionate product and calcium oxide precipitate out, and the precipitate is dried. Then the remaining water and any un-reacted propionic acid are centrifuged out of the precipitate. The dried product is then ground, and is ready for use as a feed additive or feed supplement, with a minimum of 10% active chromium content, i.e. bio-available Cr(II).

In one specific example, one kilogram of propionate-based chromium chelate is prepared from starting materials include chromium carbonate, $Cr_2(CO_3)_3$, in an amount 315 g; calcium oxide CaO in an amount 225 g; propionic acid, $CH_3CH_2COOH$ in an amount of about 570 grams; and water in an amount of 150 ml.

An amount of 315 grams of the chromium carbonate was weighed, and placed in a glass or stainless steel vessel, and 150 milliliters of water was added into the vessel. These ingredients were mixed thoroughly to form a paste. Then 570 grams of propionic acid was measured out and added to the contents of the vessel while mixing thoroughly. Then 225 grams of calcium oxide was measured; that was added slowly while stirring the contents. Heat is generated during these phases, so proper safety precautions were observed. A chromium chelate was formed as a precipitate. The precipitate could be dried at room temperature, but in this example the material was placed in a hot air oven at about 80° C. for 3 to 4 hours. The drying can include a centrifugation step to remove excess water and unreacted acid.

The dried material was ground up in a lab grinder and placed in a suitable air-tight container.

The specifications of the finished product were tested and found to satisfy a maximum moisture content of 5.0% and a minimum chromium content of 10.0%, which can then be blended in a suitable amount into an animal feed.

While a batch process was used to produce the final product in this example, a continuous process can be easily developed to process these same starting materials and yield the same final chromium propionate product.

While the invention has been described with reference to specific examples and embodiments, the invention is not to be limited to those embodiments, but the scope of the invention is to be ascertained from the appended claims.

What is claimed is:

1. Process for forming chromium propionate in suitable form for use as an agricultural feed additive containing a minimum of 10% available chromium(III) and essentially free of hexavalent chromium, the process comprising:
    a) into a vessel adding a quantity of chromium carbonate, and introducing a sufficient quantity of water to form an aqueous paste consisting essentially of the water and the chromium carbonate;
    b) adding to said aqueous paste in said vessel a quantity of propionic acid while stirring the paste and added propionic acid;
    c) adding to said paste of step b) a quantity of one of calcium oxide and magnesium oxide sufficient to raise the pH of said paste to a basic level to permit exothermal reaction of the chromium carbonate with the propionic acid to form chromium (III) propionate;
    d) allowing the chromium carbonate, propionic acid, and said one of calcium oxide and magnesium oxide to react to completion resulting in a precipitate of chromium (III) propionate and reaction byproducts of said one of calcium oxide and magnesium oxide;
    e) placing the precipitate of step d) into a drying device and removing residual water remaining therein after step d) to dry the precipitate, such that the reaction byproduct of the one of the calcium oxide and magnesium oxide includes a carbonate salt that serves as an anti-caking agent; and
    f) comminuting the dried precipitate to a desired particle size.

2. Process for forming chromium propionate according to claim 1, wherein said one of calcium oxide and magnesium oxide is calcium oxide.

3. Process for forming chromium propionate according to claim 1, wherein the reaction in steps a) to d) is exothermic and generates sufficient heat to evaporate most of the water from the precipitate of step d), such that the steps a) through c) are carried out without externally added heat.

4. Process for forming chromium propionate according to claim 1, wherein the steps a) through d) are carried out in absence of a catalyst.

5. Process for forming chromium propionate according to claim 1, wherein said drying device is a centrifuge and said removing of residual water is carried out by centrifugation.

6. Process for forming chromium propionate according to claim 1, wherein said chromium carbonate is added in an amount of about 1,000 g to 1,200 g per each liter of water, and said propionic acid is added in an amount that is molar equivalent to said chromium carbonate.

7. Process for forming chromium propionate according to claim 6, wherein said propionic acid is added in an amount of about 2,300 g per each liter of water.

8. Process for forming chromium propionate according to claim 7, wherein said step d) includes adding a quantity of calcium oxide in an amount of about 900 g per each liter of water.

9. Process for forming chromium propionate according to claim 1, further comprising blending the comminuted chromium propionate in suitable amount into an animal feed.

10. Process for forming chromium propionate according to claim 1, wherein the process is carried out in the absence of sodium hydroxide.

* * * * *